United States Patent
Dib

(10) Patent No.: US 8,798,721 B2
(45) Date of Patent: Aug. 5, 2014

(54) SYSTEM AND METHOD FOR VISUALIZING CATHETER PLACEMENT IN A VASCULATURE

(75) Inventor: Nabil Dib, Paradise Valley, AZ (US)

(73) Assignee: Dib Ultrasound Catheter, LLC, Gilbert, AZ (US)

( * ) Notice: Subject to any disclaimer, the term of this patent is extended or adjusted under 35 U.S.C. 154(b) by 512 days.

(21) Appl. No.: 12/788,194

(22) Filed: May 26, 2010

(65) Prior Publication Data
US 2011/0295106 A1 Dec. 1, 2011

(51) Int. Cl.
*A61B 5/05* (2006.01)
*A61B 19/00* (2006.01)
*A61M 25/01* (2006.01)

(52) U.S. Cl.
CPC ..... *A61B 19/5244* (2013.01); *A61B 2019/5263* (2013.01); *A61M 2025/0166* (2013.01)
USPC ........... 600/424; 600/434; 600/435; 600/439; 604/19

(58) Field of Classification Search
USPC ......... 600/407, 411, 424, 427, 433, 434, 435, 600/437, 462, 463, 466, 467; 606/41, 44, 606/46, 253, 325
See application file for complete search history.

(56) References Cited

U.S. PATENT DOCUMENTS

| | | | |
|---|---|---|---|
| 3,659,610 A | 5/1972 | Cimber | |
| 5,115,814 A * | 5/1992 | Griffith et al. | 600/463 |
| 5,139,496 A | 8/1992 | Hed | |
| 5,901,895 A * | 5/1999 | Heaton et al. | 227/176.1 |
| 6,106,518 A | 8/2000 | Wittenberger et al. | |
| 6,547,788 B1 * | 4/2003 | Maguire et al. | 606/41 |
| 6,640,120 B1 | 10/2003 | Swanson et al. | |
| 6,733,499 B2 | 5/2004 | Scheib | |
| 6,824,543 B2 | 11/2004 | Lentz | |
| 6,869,431 B2 | 3/2005 | Maguire et al. | |
| 6,926,711 B2 | 8/2005 | Lentz et al. | |
| 7,008,418 B2 | 3/2006 | Hall et al. | |
| 7,089,063 B2 | 8/2006 | Lesh et al. | |
| 7,621,925 B2 * | 11/2009 | Saadat et al. | 606/139 |
| 2003/0144671 A1 * | 7/2003 | Brooks et al. | 606/108 |
| 2004/0243118 A1 | 12/2004 | Ayers et al. | |
| 2005/0222518 A1 * | 10/2005 | Dib | 600/562 |
| 2006/0178586 A1 * | 8/2006 | Dobak, III | 600/508 |
| 2006/0265000 A1 * | 11/2006 | Azizi | 606/200 |
| 2007/0038110 A1 * | 2/2007 | Flesch et al. | 600/459 |
| 2007/0038121 A1 | 2/2007 | Feldman et al. | |
| 2007/0239105 A1 | 10/2007 | Weitzner et al. | |
| 2008/0103361 A1 * | 5/2008 | Makower et al. | 600/115 |
| 2008/0269876 A1 * | 10/2008 | Huynh et al. | 623/2.11 |
| 2009/0131790 A1 * | 5/2009 | Munrow et al. | 600/439 |
| 2009/0209950 A1 * | 8/2009 | Starksen | 606/21 |

* cited by examiner

Primary Examiner — Unsu Jung
Assistant Examiner — Michael N Fisher
(74) Attorney, Agent, or Firm — Nydegger & Associates

(57) ABSTRACT

A system for advancing a needle through a vasculature to an injection site at the heart of a patient includes a guide catheter with a reflective distal tip. Also included is an imaging unit that is mounted on the catheter to radiate an energy field. Structurally, a distal portion of the catheter is biased to bend into a predetermined configuration that will position the distal end of the catheter for interception by the energy field. If necessary, coincidence of the reflective tip with the energy field is established by moving the energy field along the length of the guide catheter. With coincidence, the reflective tip reflects a signal that is useful for advancement of the needle from the guide catheter and into the injection site.

15 Claims, 2 Drawing Sheets

SYSTEM AND METHOD FOR VISUALIZING CATHETER PLACEMENT IN A VASCULATURE

FIELD OF THE INVENTION

The present invention pertains generally to systems for advancing a needle through the vasculature of a patient to an injection site at the heart. More particularly, the present invention pertains to systems that incorporate an imaging modality, such as ultrasound (US) or Optical Coherence Tomography (OCT), to image needle or wire placement in the vasculature. The present invention is particularly, but not exclusively, useful as a system and method for bringing the energy field of an imaging modality into coincidence with the distal end of a catheter, to monitor the advancement of a needle or wire from the distal end of the catheter.

BACKGROUND OF THE INVENTION

Intravascular operations are always complicated by the simple fact that there is typically no direct visual contact with the instruments that are being used to perform the operation. To help overcome this inconvenience, several effective imaging modalities have been developed for use in the vasculature. For example, ultrasound technology is a well established imaging modality that has proven useful for many applications inside a body. Optical Coherence Tomography (OCT) is another accepted imaging modality. These imaging modalities, however, have their respective unique, operational limitations that must be accounted for. In particular, the energy fields that are used by the imaging modalities must somehow be made incident on the target area that is to be imaged, and instruments to be used in the target area must be observable.

It happens that many intravascular operations can be relatively easily accomplished. Moreover, they can often be done with minimal structural manipulations. As an example, the delivery of biologics (e.g. cells, genes, protein and drugs) to a selected injection site can be easily accomplished by using a needle injector. For such an operation, however, it is essential to properly position the instrument that is being used (e.g. a needle injector). In particular, for instances wherein an imaging modality is being used to position an instrument, the energy field of the imaging modality must be positioned to both cover the injection site, and intercept (i.e. become coincident with) the instrument.

With the above in mind, it is an object of the present invention to provide a navigation system for use in advancing a needle or a wire (i.e. a guide wire) to an injection site at the heart of a patient which reconfigures a guide catheter to position its distal tip for visualization by an imaging unit. Another object of the present invention is to provide a navigation system, for use when advancing a needle or wire through the vasculature of a patient, that provides for the movement of an imaging unit so its energy field will intercept the distal tip of a guide catheter for visualization of the catheter tip at an injection site. Yet another object of the present invention is to provide a navigation system for use in advancing a needle or wire to an injection site in the vasculature or at the heart of a patient which is simple to manufacture, is easy to use, and is cost effective.

SUMMARY OF THE INVENTION

A system in accordance with the present invention is provided for advancing a needle to an injection site in the vasculature or at the heart of a patient. The system essentially includes a guide catheter and an imaging unit that is associated with the guide catheter. In more detail, the guide catheter has a reflective distal tip, and the imaging unit radiates an energy field in a substantially radial direction from the axis of the guide catheter for the purpose of locating the tip.

Insofar as structure of the guide catheter is concerned, a distal portion of the guide catheter is biased to bend into a predetermined configuration (i.e. the guide catheter may have a pre-bent portion). As envisioned for the present invention, this configuration will position the distal end of the catheter in the vasculature for interception by the energy field. If necessary, a coincidence of the reflective tip with the energy field can be established by manipulation of an actuator. Specifically, such a manipulation will move the energy field axially along the length of the guide catheter to intercept the reflective distal tip of the catheter. Once there is coincidence (i.e. when the reflective tip of the guide catheter is located and visualized in the energy field), the reflective tip will reflect a signal. Importantly, this reflective signal is useful for further positioning of the distal tip and for advancing the needle from the guide catheter and into the injection site. For an alternate embodiment of the present invention, the distal portion of the catheter can be steerable, rather than being pre-bent.

Structurally, the guide catheter defines an axis and it has a proximal end and a distal end. It also has a lumen that extends between the proximal and distal ends of the guide catheter. Further, the lumen is dimensioned to receive either a needle injector that includes a needle for injection into the myocardium, or a wire that passes through the lumen of the catheter to navigate the vasculature, such as by crossing heart valves or septal defects. An extracorporeal source of a fluid (e.g. biologics: cells, genes, protein and drugs) is attached to the proximal end of the injector for delivery through the needle.

An important structural aspect of the present invention is that the distal portion of the guide catheter is formed with a bendable section. Specifically, at least one part in the bendable section is biased to be bent through an angle $\theta$. In an alternate embodiment, there can also be a second part in the bendable section that is further biased to bend through an angle $\phi$. For the alternate embodiment, the center of rotation for the angle $\theta$ is axially opposite the center of rotation for the angle $\phi$. Stated differently, the bendable section can be simultaneously bent in two different directions. Further, a reflective tip is attached to the bendable section at the distal end of the guide catheter, and a handle is affixed to the proximal end of the guide catheter.

Mounted on the guide catheter is an imaging unit that interacts with the reflective tip of the guide catheter to visualize the tip's location in the vasculature. In detail, the imaging unit includes a generator, a detector, and a transceiver that is mounted for axial movement on the guide catheter. Further, the imaging unit includes an actuator that is positioned in the handle of the guide catheter to move the transceiver axially along the guide catheter. The actuator will typically have a dial that is mounted on the handle, and it will include an activation wire wherein a first end of the activation wire is attached to the transceiver and a second end is engaged with the dial. Manipulation of the dial will then produce an axial movement of the transceiver along the guide catheter. Structurally, the operative components of the actuator can be selected as any one of several well-known types, such as a rack and pinion, a lead screw or a reel.

Operationally, the system of the present invention will use the generator, in combination with the transceiver, to radiate an energy field into the vasculature. This radiation will typically be in a substantially radial direction from the axis of the guide catheter. Preferably, the generator will generate ultrasound energy, but, it is well known that OCT systems can also be effective for purposes of the present invention. In either case, when the reflective tip is in the energy field, energy (e.g. ultrasound energy) will be reflected from the tip. Also, the energy will be reflected by target tissue, such as the heart. A detector that is electronically connected to the transceiver will then receive and evaluate the signal of reflected energy to determine where exactly the reflective tip is located, relative to target tissue (e.g. heart), in the energy field. The needle injector can then be advanced through the lumen of the guide catheter for extension of the needle beyond the reflective tip and from the distal end of the guide catheter for use at an injection site. As indicated above, a guide wire, rather than the needle injector, may be advanced through the catheter.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
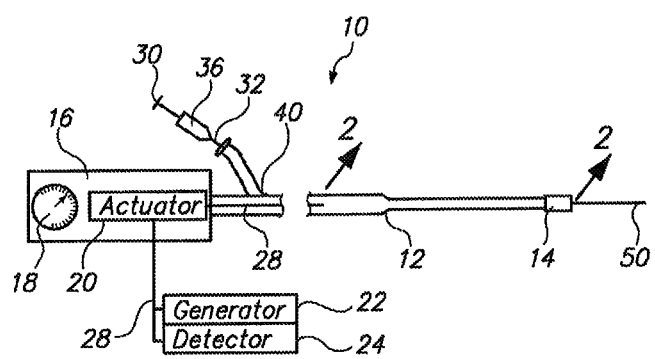
FIG. 1 is a schematic drawing of a system in accordance with the present invention.

Referring initially to FIG. 1, a system in accordance with the present invention is shown and is generally designated 10. As shown, the system 10 includes a guide catheter 12 that has a reflective tip 14 at its distal end. The system 10 also has a handle 16 that is mounted at the proximal end of the guide catheter 12, with a dial 18 and an actuator 20 being included as part of the handle 16. Structurally, the dial 18 is connected directly to the actuator 20 for manipulating the actuator 20 during an operation of the system 10. FIG. 1 further indicates that the system 10 includes an energy generator 22 and a detector 24. More specifically, with cross reference to FIG. 2, it is to be appreciated that both the energy generator 22 and the detector 24 are electronically connected to a transceiver 26 via an activation wire 28. It is also to be appreciated that the activation wire 28 can be manipulated by the actuator 20 to move the transceiver 26. Collectively, the energy generator 22, detector 24 and the transceiver 26 are hereinafter sometimes referred to as an imaging unit.

Still referring to FIG. 1, it will be seen that the guide catheter 12 is to be used with a needle injector 30. More specifically, the needle injector 30 includes a needle wire 32 that has a needle 34 formed at its distal end (see FIG. 2). A fluid source 36 is also provided for the injector 30, and this source 36 will typically hold a fluid that includes biologics (e.g. cells, genes, protein and drugs) for delivery through the injector 30. As shown, access into the lumen 38 (see FIG. 2) of the guide catheter 12 for both the needle 34 and the needle wire 32 of the injector 30 is provided via a y-site 40.

Figure 2:
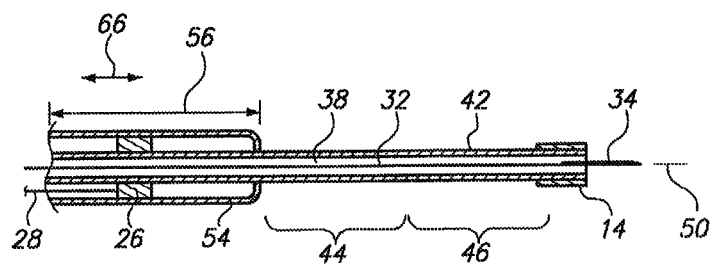
FIG. 2 is a cross sectional view of the distal portion of the guide catheter of the present invention as seen along the line 2-2 in FIG. 1.
Figure 3A:
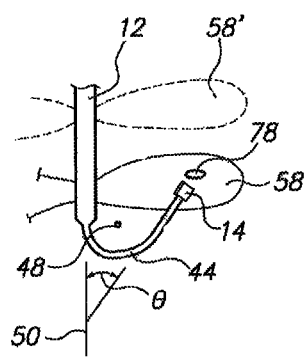
FIG. 3A is a view of the distal portion of the guide catheter shown in its operational environment and configured with a single bend used for positioning the catheter's distal end at an injection site.
Figure 3B:
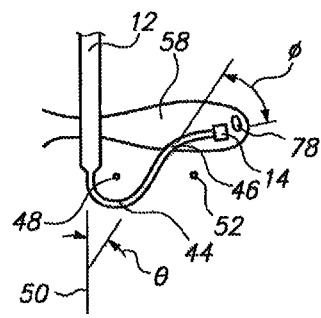
FIG. 3B is a view of the distal portion of the guide catheter shown in its operational environment and configured with a double bend used for positioning the catheter's distal end at an injection site.

An important structural aspect of the guide catheter 12 is its ability to be reconfigured. This will be best appreciated with reference to FIG. 2, along with reference to FIGS. 3A and 3B. In FIG. 2 it is shown that a bendable section 42, at the distal portion of the guide catheter 12, can be considered as having at least one reconfigurable part 44. Alternatively, there can be an additional reconfigurable part 46. Consider first, a structure for the guide catheter 12 wherein there is no part 46 and, instead, only a part 44. With reference to FIG. 3A, it will be seen that for this embodiment of the guide catheter 12, the bendable section 42 can be biased to bend around a center of curvature 48 to establish an angle $\theta$. As shown, the angle $\theta$ is measured relative to an axis 50 that is generally defined by the length of the guide catheter 12. On the other hand, as shown in FIG. 3B, when parts 44 and 46 are both incorporated into the bendable section 42 of the guide catheter 12, the bendable section 42 can be respectively biased to rotate through the angle $\theta$ and, additionally, through an angle $\phi$ around a center of curvature 52. As shown, the angles $\theta$ and $\phi$ are measured in opposite directions with their respective centers of curvature 48 and 52 on opposite sides of the axis 50. In addition to providing for structural biasing in the bendable section 42, it is well known that various devices have been proposed for bending or steering a catheter through the vasculature of a patient (not shown). For purposes of the present invention, any such device would be suitable for reconfiguring the guide catheter 12.

Another structural aspect of the guide catheter 12 that is of more general importance for the entirety of the system 10 concerns the actuator 20. More specifically, the manipulation of the imaging unit and the consequent movement of the transceiver 26 is essential for the operation of the system 10. This aspect will be best appreciated by sequentially cross referencing FIG. 2 with FIGS. 4A, 4B and 4C. Specifically, this aspect regards movements of the transceiver 26 along the axis 50 of the guide catheter 12.

With reference to FIG. 2 it will be noted that, proximal to its bendable section 42, the guide catheter 12 is formed with a sleeve 54. Further, it is to be understood that the transceiver 26 is moveable inside the sleeve 54 by a manipulation of the actuator 20. More specifically, movements of the transceiver 26 by the actuator 20 are made on the guide catheter 12, through a range 56, in directions back and forth along the axis 50 indicated by arrows 66. The real purpose here is to move an energy field 58 that is radiated from the transceiver 26. In detail, the energy field 58 will be primarily oriented in a direction perpendicular to the axis 50, and will be radiated whenever the transceiver 26 is activated by the generator 22. As envisioned for the present invention, although the generator 22 will preferably generate ultrasound energy, any other type of energy field that is known for use as an imaging modality is suitable (e.g. OCT). Further, although a two-dimensional field of ultrasound energy is typical, a three dimensional ultrasound field may also be used.

Figure 4A:
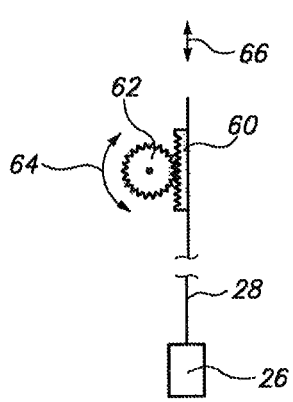
FIG. 4A shows a rack and pinion arrangement for the actuator of the present invention.
Figure 4B:
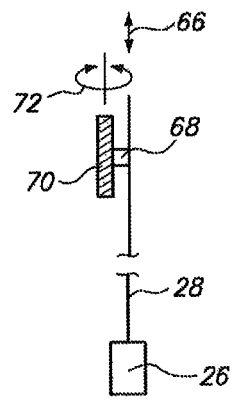
FIG. 4B shows a lead screw arrangement for the actuator of the present invention.
Figure 4C:
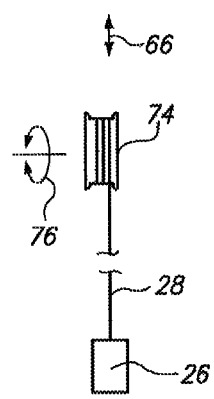
FIG. 4C shows a reel arrangement for the actuator of the present invention.

In accordance with the system 10, several different types of mechanisms can be incorporated into the actuator 20 for the purpose of moving the energy field 58 (i.e. transceiver 26). The mechanisms shown in FIGS. 4A, 4B and 4C are only exemplary. In FIG. 4A, the components for the actuator 20 are shown to include a straight toothed rack 60 that is affixed to the activation wire 28. A pinion 62 is shown engaged with the rack 60 and, with this engagement, the pinion 62 can be rotated by the dial 18 on handle 16 in the directions indicated by arrows 64. This rotation of the pinion 62 will then move the transceiver 26 axially along the guide catheter 12 in the directions of arrows 66. In another arrangement of components for the actuator 20 shown in FIG. 4B, a projection 68 is affixed to the activation wire 28. A lead screw 70 is then engaged with the projection 68. Consequently, a rotation of the lead screw 70 by the dial 18 in directions indicated by arrows 72 will move the transceiver 26 axially along the guide catheter 12 in the directions of arrows 66. Further, in another embodiment of components for the actuator 20 shown in FIG. 4C, a reel 74 is incorporated to take-up the activation wire 28. More specifically, with a rotation of the reel 74 in the directions indicated by arrows 76, the transceiver 26 will move axially along the guide catheter 12 in the directions of arrows 66.

For an operation of the system 10, the guide catheter 12 is positioned in the vasculature of a patient (not shown), and there it is reconfigured as shown in either FIG. 3A or FIG. 3B. The transceiver 26 can then be moved by the actuator 20, as disclosed above, so that the energy field 58 radiated by the transceiver 26 will intercept the reflective tip 14 of the guide catheter 12. For example, such a movement of the energy field 58 is shown in FIG. 3A where it can be seen that the energy field 58' has been moved axially along the guide catheter 12 to a new position for the energy field 58. Once there is coincidence (i.e. the reflective tip 14 of the guide catheter 12 is located in the energy field 58, and can be visualized with the detector 24 of the particular imaging modality being used), the reflective tip 14 can be further manipulated. Also, in this configuration the reflective tip 14 is positioned so that an advancement of needle 34 (or a guide wire) from reflective tip 14 will be seen as an axial movement of the needle 34. Further, because the energy field 58 will also see an injection site 78 on target tissue (e.g. the heart), advancement of the needle 34 can be made relative to the injection site 78 (target tissue). In particular, this additional manipulation may be necessary in order to properly position the tip 14 at a predetermined injection site 78. The needle injector 30 can then be advanced through the guide catheter 12 to perform an injection with the needle 34 at the injection site 78.

While the particular System and Method for Visualizing Catheter Placement in a Vasculature as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A navigation system for use in advancing a needle through a vasculature to an injection site at the heart of a patient which comprises:
   a guide catheter defining an axis and having a proximal end and a distal end, wherein the guide catheter is reconfigurable and is formed with a lumen extending between the ends thereof for advancing the needle through the lumen of the guide catheter, and wherein the guide catheter has a bendable section located along a distal portion of the guide catheter;
   a reflective tip attached to the bendable section at the distal end of the guide catheter;
   a transceiver integrated with the guide catheter and mounted for axial movement back and forth along the guide catheter to radiate an energy field in a radial direction from the axis of the guide catheter; and
   an actuator configured to move the transceiver to intercept reflected energy from the reflective tip on the guide catheter to create a signal from the reflective tip on the guide catheter, for receipt by the transceiver on the guide catheter, to determine where the reflective tip is located in the energy field, to reconfigure the guide catheter and position the distal tip for advancing the needle from the guide catheter into the injection site.

2. A system as recited in claim 1 further comprising a needle injector, wherein the needle injector can be advanced through the lumen of the guide catheter for extension of the needle beyond the reflective tip at the distal end of the guide catheter.

3. A system as recited in claim 1 further wherein the bendable section of the guide catheter is pre-bent.

4. A system as recited in claim 3 wherein the actuator comprises:
   a handle affixed to the proximal end of the guide catheter;
   a dial mounted on the handle; and
   an activation wire having a first end and a second end, wherein the first end is attached to the transceiver and the second end is engaged with the dial to provide for axial movement of the transceiver along the guide catheter in response to manipulation of the dial.

5. A system as recited in claim 4 wherein the actuator further comprises:
   a straight toothed rack affixed to the activation wire; and
   a pinion affixed to the dial, wherein the pinion interacts with the rack to provide for an axial movement of the activation wire in response to a rotation of the pinion by manipulation of the dial.

6. A system as recited in claim 4 wherein the actuator further comprises:
   a projection affixed to the activation wire; and
   a lead screw affixed to the dial, wherein the lead screw interacts with the projection to provide for an axial movement of the activation wire in response to a rotation of the lead screw by manipulation of the dial.

7. A system as recited in claim 4 wherein the actuator further comprises a reel affixed to the dial, wherein the reel is mounted for rotation on the handle to receive the activation wire and provide for an axial movement of the activation wire in response to a rotation of the reel by manipulation of the dial.

8. A system as recited in claim 1 wherein the bendable section of the guide catheter is biased to be bent around a center of rotation through an angle $\theta$ to position the reflective tip in the energy field.

9. A system as recited in claim 8 wherein the center of rotation for the angle $\theta$ is a first center of rotation, and a first part of the bendable section is bent through the angle $\theta$, and wherein a second part of the bendable section is further biased to bend around a second center of rotation through an angle $\phi$, and further wherein the first center of rotation is axially opposite the second center of rotation.

10. A navigation system for use in advancing a needle through the vasculature to an injection site at the heart of a patient which comprises:
    a guide catheter defining an axis and having a proximal end and a distal end, wherein the guide catheter is reconfigurable and is formed with a lumen extending between the ends thereof for receiving an advancement of the needle through the lumen of the guide catheter, and with a bendable section located along a distal portion of the guide catheter;
    a reflective tip attached to the bendable section at the distal end of the guide catheter;

a transceiver integrated with the guide catheter and mounted for axial movement back and forth along the guide catheter without blocking the guide catheter lumen to radiate an energy field in a radial direction from the axis of the guide catheter; and an actuator configured to axially move the transceiver along the guide catheter to intercept reflected energy from the reflective tip on the guide catheter to create a signal from the reflective tip on the guide catheter, for receipt by the transceiver on the guide catheter, to determine where the reflective tip is located in the energy field, to reconfigure the guide catheter and position the distal tip for advancing the needle from the guide catheter into the injection site.

11. A system as recited in claim 10 further comprising a needle injector configured to manipulate the needle, wherein the needle injector can be advanced through the lumen of the guide catheter for extension of the needle beyond the reflective tip at the distal end of the guide catheter.

12. A system as recited in claim 10 wherein the actuator comprises:
   a handle affixed to the proximal end of the guide catheter;
   a dial mounted on the handle; and
   an activation wire having a first end and a second end, wherein the first end is attached to the transceiver and the second end is engaged with the dial to provide for axial movement of the transceiver along the guide catheter in response to manipulation of the dial.

13. A system as recited in claim 10 wherein the bendable section comprises:
   a first part, wherein the first part is biased to bend through an angle θ; and
   a second part, wherein the second part is biased to bend through an angle ϕ, wherein the angles θ and ϕ bend in opposite directions.

14. A navigation system for use in advancing a needle to an injection site at the heart of a patient which comprises:
   a catheter means for defining an axis and having a proximal end and a distal tip, wherein the catheter means is reconfigurable, with a bendable section located along a distal portion of the catheter; and
   a means for imaging integrated with the catheter means and mounted on the catheter means for radiating an energy field in a radial direction from the axis of the catheter means, wherein the imaging means on the catheter means can be selectively positioned back and forth along the axis of the catheter means to intercept reflected energy from the distal tip of the catheter means to create a signal for use in reconfiguring the catheter means and positioning the distal tip thereof to image an advancement of the needle from the distal tip into the injection site.

15. A system as recited in claim 14 wherein the catheter means comprises:
   a reflective tip attached to the bendable section at the distal end of the catheter means, wherein the bendable section of the guide catheter can be reconfigured to position the reflective tip in the energy field to create a signal from the reflective tip, for receipt by the imaging means to determine where the reflective tip is located in the energy field;
   a handle affixed to the proximal end of the catheter means;
   a dial mounted on the handle; and
   an activation wire having a first end and a second end, wherein the first end is attached to the imaging means and the second end is engaged with the dial to provide for axial movement of the imaging means along the catheter means in response to manipulation of the dial.

* * * * *